United States Patent [19]
Viitala et al.

[11] Patent Number: 6,113,575
[45] Date of Patent: Sep. 5, 2000

[54] VOLUME CONTROL APPARATUS FOR A FLEXIBLE VENOUS RESERVOIR

[75] Inventors: Daniel W. Viitala, Dexter; Erin J. Lindsay, Manchester, both of Mich.

[73] Assignee: Terumo Cardiovascular Systems Corporation, Somerset, N.J.

[21] Appl. No.: 09/079,046

[22] Filed: May 14, 1998

[51] Int. Cl.[7] .................................................. A61M 37/00
[52] U.S. Cl. ............................................................ 604/132
[58] Field of Search ................................... 604/132, 407, 604/151, 153, 246, 249

[56] References Cited

U.S. PATENT DOCUMENTS

| | | |
|---|---|---|
| 3,276,589 | 10/1966 | Jankay . |
| 3,545,671 | 12/1970 | Ross . |
| 3,565,292 | 2/1971 | Jinotti . |
| 3,595,232 | 7/1971 | Leibinsohn . |
| 3,625,401 | 12/1971 | Terry . |
| 3,642,047 | 2/1972 | Waage . |
| 3,734,351 | 5/1973 | Gaudin . |
| 3,902,635 | 9/1975 | Jinotti . |
| 3,907,504 | 9/1975 | Hammond et al. . |
| 3,992,706 | 11/1976 | Tunney et al. . |
| 4,004,590 | 1/1977 | Muriot . |

(List continued on next page.)

FOREIGN PATENT DOCUMENTS

| | | |
|---|---|---|
| 0 080 610 B1 | 2/1986 | European Pat. Off. . |
| 0 198 869 B1 | 12/1988 | European Pat. Off. . |
| 0 342 404 A2 | 11/1989 | European Pat. Off. . |
| 0 348 682 B1 | 8/1992 | European Pat. Off. . |
| 0 401 016 B1 | 4/1994 | European Pat. Off. . |
| 2 102 412 | 4/1972 | France . |
| 2 584 608 | 1/1987 | France . |
| 61-257659 | 11/1986 | Japan . |
| 7708421 | 7/1977 | Netherlands . |
| 2 245 176 | 1/1992 | United Kingdom . |
| WO 86/02825 | 5/1986 | WIPO . |
| WO 94/08645 | 4/1994 | WIPO . |
| WO 95/07725 | 3/1995 | WIPO . |
| WO 96/35462 | 11/1996 | WIPO . |

OTHER PUBLICATIONS

Terumo "CAPIOX SX Seriers Oxygenators".
"Blood Component Therapy", Fenwal Laboratories, Farmington, Massachusetts.
"COBE VRB 1200" COBE Closed Venous Reservoir Bag, Instructions for Use, Catalog No. 1050–250–000.
MONOLYTH, Monolyth Integrated Membrane Lung, SORIN Biomedical.
3M Sarns, "turbo 440 Membrane Oxygenator", 3M Health Care.
Hollow Fiber Oxygenator CAPIOX SX, Instructions for Use, Terumo.
Maxima Forte™ Hardshell Venous Reservoir, Medtronic.
Maxima® Hardshell™ Venous Reservoir, Medtronic.
Sarns SMO/INF Infant Membrane Oxygenator, 3M Health Care.
The BMR–1900 Venous Reservoir, Baxter.
Sarns™ 9440, 3M pamphlet.
Sarns™ Turbo ICR Holder 5860, 3M Health Care pamphlet.
Sarns™ Adjustable Holders for Oxygenator and Reserviors, 3M Health Care pamphlet.

*Primary Examiner*—Gene Mancene
*Assistant Examiner*—Eduardo C. Robert
*Attorney, Agent, or Firm*—Burns, Doane, Swecker & Mathis, LLP

[57] ABSTRACT

A volume controlling support for a flexible venous reservoir that permits the reservoir to have a clear flow passage from its inlet to its outlet which is visible and accessible to the perfusionist. The portion of the reservoir through which the major part of the blood flow is occurring can be manipulated if necessary, particularly for the purpose of manipulating the reservoir to improve the clearance of air bubbles in the blood. Preferred embodiments also enhance the convenience for the perfusionist by permitting right-handed or left-handed operation, and by providing an approximate read-out of the volume of blood contained in the reservoir.

51 Claims, 8 Drawing Sheets

U.S. PATENT DOCUMENTS

| | | |
|---|---|---|
| 4,019,656 | 4/1977 | Spears . |
| 4,019,707 | 4/1977 | Quinn et al. . |
| 4,058,363 | 11/1977 | Silbert . |
| 4,085,866 | 4/1978 | Fekl . |
| 4,157,771 | 6/1979 | Smith . |
| 4,187,845 | 2/1980 | Dror . |
| 4,284,209 | 8/1981 | Barbour, Jr. . |
| 4,316,576 | 2/1982 | Cullis et al. . |
| 4,378,014 | 3/1983 | Elkow . |
| 4,393,880 | 7/1983 | Taylor . |
| 4,447,939 | 5/1984 | Taylor . |
| 4,451,259 | 5/1984 | Geissler et al. . |
| 4,466,888 | 8/1984 | Verkaart . |
| 4,496,354 | 1/1985 | Steer et al. . |
| 4,500,308 | 2/1985 | Kurtz et al. . |
| 4,500,311 | 2/1985 | Redmond et al. . |
| 4,557,728 | 12/1985 | Sealfon et al. . |
| 4,573,992 | 3/1986 | Marx . |
| 4,626,243 | 12/1986 | Singh et al. . |
| 4,717,377 | 1/1988 | Fukasawa . |
| 4,830,510 | 5/1989 | Bellhouse . |
| 4,857,042 | 8/1989 | Schneider . |
| 4,943,288 | 7/1990 | Kurtz et al. . |
| 4,976,707 | 12/1990 | Bodicky et al. . |
| 4,976,851 | 12/1990 | Tanokura et al. . |
| 4,991,743 | 2/1991 | Walker . |
| 4,994,021 | 2/1991 | Smith et al. . |
| 5,049,146 | 9/1991 | Bringham et al. . |
| 5,061,451 | 10/1991 | Ganshirt et al. . |
| 5,078,677 | 1/1992 | Gentelia et al. . |
| 5,262,070 | 11/1993 | Ishida . |
| 5,281,202 | 1/1994 | Weber et al. ............... 604/132 |
| 5,352,218 | 10/1994 | Buckley et al. . |
| 5,374,257 | 12/1994 | Drainville et al. . |
| 5,411,482 | 5/1995 | Campbell ............... 604/153 |
| 5,484,428 | 1/1996 | Drainville et al. . |
| 5,573,526 | 11/1996 | Hess . |
| 5,693,039 | 12/1997 | Stewart et al. . |
| 5,720,741 | 2/1998 | Stewart et al. . |

VOLUME CONTROL APPARATUS FOR A FLEXIBLE VENOUS RESERVOIR

TECHNICAL FIELD

The invention relates generally to the practice of cardiac surgery, and more specifically to an apparatus for managing venous blood being returned from the body and/or from a cardiotomy device.

BACKGROUND OF THE INVENTION

When the heart is stopped during cardiovascular surgery, it is necessary to provide for the function of the heart and/or the lungs artificially. The patient's blood is conducted out of the body from the venous system for oxygenation and filtration and is then pumped back into the body and the arterial system. Such extracorporeal arrangements typically include a reservoir, typically called a venous reservoir, to store a certain volume of blood. Often, the reservoir receives blood from the main attachment to the venous circulation, and "cardiotomy" blood collected by suction from the surgical site. The venous reservoir provides a volume buffer for the extracorporeal system, and also a measure of air bubble removal.

It is known to provide venous reservoirs with rigid walls, and also to provide venous reservoirs which have flexible walls. Flexible venous reservoirs, constructed in the form of a bag or pouch of flexible, polymeric material have the advantage of providing a smooth, even flow of blood from an inlet to an outlet. This is useful since blood is a fragile substance, and likely to be adversely affected if allowed to lie stagnant in any portion of the extracorporeal circuit. Flexible venous reservoirs typically have one or more vents at the top to allow the venting off of gas bubbles which have entered the blood upstream of the reservoir (e.g., in the cardiotomy blood).

It is also known that it can be advantageous to support a flexible venous reservoir in an assembly which physically constrains the flexible walls of the reservoir so as to limit the maximum blood volume which may be contained in the reservoir. One such arrangement is disclosed in U.S. Pat. Nos. 5,352,218; 5,693,039 and 5,720,741, where a flexible venous reservoir is constrained between a bracket frame and a front plate. However, in the disclosed arrangement, the front plate covers substantially the entire front and back surface of the flexible reservoir, leaving no access to the reservoir for manipulation to expedite air bubble removal without releasing the entire reservoir from restraint.

U.S. Pat. No. 5,573,526 discloses another flexible reservoir and a volume restricting holder assembly comprising a rigid base plate and a volume restriction plate, which define a V-shaped gap of variable size for receiving the flexible reservoir.

SUMMARY OF THE INVENTION

In one of its aspects, the invention provides a volume controlling support for a flexible venous reservoir that permits the reservoir to have a clear flow passage from its inlet to its outlet which is visible and accessible to the perfusionist. Unlike known arrangements, the portion of the reservoir through which the major part of the blood flow is occurring can be manipulated if necessary, particularly for the purpose of manipulating the reservoir to improve the clearance of air bubbles in the blood. Preferred embodiments also enhance the convenience for the perfusionist by permitting right-handed or left-handed operation, by providing an approximate read-out of the volume of blood contained in the reservoir, and/or by permitting operation with different size flexible venous reservoirs.

A first aspect of the invention is a combination of a flexible venous reservoir and a volume controlling apparatus. The flexible reservoir comprises flexible walls defining a blood storage chamber having an upper perimeter, and an inlet and an outlet to the blood storage chamber defining a blood flow path through the blood storage chamber between the inlet and outlet. The volume controlling apparatus comprises a panel, a pressure plate, and adjustable mounting means for movably mounting the pressure plate on the panel so that the flexible venous reservoir can be positioned between the panel and the pressure plate and in contact with both to adjustably limit the maximum volume of the flexible venous reservoir. The pressure plate is sized relative to the blood storage chamber such that a significant blood flow passage remains uncovered by the pressure plate along the upper perimeter of the blood storage chamber from the inlet to the outlet.

Preferably, the adjustable mounting means comprises a cross arm having one end connected to the pressure plate, and a position regulating apparatus for moving the cross arm relative to the panel and holding the cross arm in position.

Most preferably, the position regulating apparatus comprises first and second arms, and a lead screw. The first and second arms are pivotably connected together at one end of each of the first and second arms, with the first arm being mounted to the panel and the second arm being mounted to the cross arm. The lead screw engages the first and second arms to pivot the second arm relative to the first arm as the lead screw is turned to move the cross arm and pressure plate relative to the panel.

Also, preferably, the position regulating apparatus further includes a knob connected to the lead screw for manually turning the lead screw, and a dial indicator connected to the lead screw so that the dial indicator rotates as the lead screw is turned. The dial indicator is marked with indicia corresponding to the approximate maximum volume permitted in the flexible venous reservoir for various positions of the pressure plate relative to the panel.

In one preferred embodiment, the lead screw engages the second arm via a trunion that is pivotably mounted to the second arm so that the trunion maintains a constant orientation relative to the first arm as the lead screw is turned. In this embodiment, the dial indicator is mounted to the trunion so that the dial indicator maintains a constant orientation relative to the first arm and panel as the second arm pivots relative to the first arm.

Preferably, the first arm comprises a mounting frame mountable in fixed relationship with the panel. The mounting frame includes two hub portions each having a through opening. The second arm constitutes a lever having first and second ends. The position regulating apparatus further comprises an axle through the lever and the through openings of the mounting frame to pivotably mount the first end of the lever on the mounting frame. The cross arm is connected to the second end of the lever, and the trunion is mounted in the lever intermediate the first and second ends thereof. Most preferably, a dial frame is provided for the indicator dial and a key-and-slot connection is provided between dial frame and trunion to mount the indicator dial on the trunion.

Also, preferably, the position regulating apparatus further includes stops that limit the range of motion of the second arm relative to the first arm, and the dial indicator rotates through no more than one full rotation throughout the range of motion of the second arm relative to the first arm.

Most preferably, the pressure plate is free to articulate relative to the cross arm to allow the pressure plate to self-level relative to the venous reservoir. For example, the pressure plate may be mounted to the cross arm by a ball-and-socket joint.

Also, preferably, a vent passageway is provided into the blood storage chamber generally adjacent the upper perimeter of the blood storage chamber for venting air bubbles from the blood storage chamber. The pressure plate is preferably generally flat and has a generally circular configuration to define the blood flow passage as generally arcuate.

Preferably, one side of the blood storage chamber is substantially covered by the pressure plate other than the blood flow passage along the upper periphery of the blood storage chamber, and the panel substantially covers the other side of the blood storage chamber at least other than the blood flow passage. It is most preferred for the panel to cover the entire back side of the blood storage chamber.

Most preferably, the pressure plate is formed of transparent material to allow the perfusionist to view the portion of the blood storage chamber covered by the pressure plate.

Also, preferably, the flexible venous reservoir and pressure plate constitute a first flexible venous reservoir and a first pressure plate, respectively. In this preferred embodiment, the combination further comprises a second flexible venous reservoir forming a different size blood storage chamber than the blood storage chamber of the first flexible venous reservoir, and a second pressure plate of different size than the first pressure plate to correspond to the size of the blood storage chamber of the second flexible venous reservoir. The first and second pressure plates are preferably interchangeably mountable by the adjustable mounting means.

In a second aspect of the invention, a volume controlling apparatus is provided for a flexible venous reservoir having flexible walls defining a blood storage chamber and an inlet and an outlet to the blood storage chamber defining a blood flow path through the blood storage chamber between the inlet and outlet. The volume controlling apparatus of the second aspect of the invention generally comprises a panel, a pressure plate, and adjustable mounting means for movably mounting the pressure plate on the panel so that the flexible venous reservoir can be positioned between the panel and the pressure plate and in contact with both to adjustably limit the maximum volume of the flexible venous reservoir. The pressure plate is free to articulate relative to the adjustable mounting means to allow the pressure plate to self-level with respect to the flexible venous reservoir.

In a third aspect of the invention, a volume controlling apparatus generally comprises a panel having opposite side edges, a pressure plate, and adjustable mounting means, attachable to the panel adjacent either side edge of the panel, for movably mounting the pressure plate on the panel so that the flexible venous reservoir can be positioned between the panel and the pressure plate and in contact with both to adjustably limit the maximum volume of the flexible venous reservoir. The adjustable mounting means comprises a cross arm having one end connected to the pressure plate, and a position regulating apparatus for moving the cross arm relative to the panel and holding the cross arm in position.

Preferably, the panel has a front side and the direction between the opposite side edges of the panel constitutes a lateral direction. Also, preferably, the cross arm is pivotable generally laterally between an operating position wherein the pressure plate is held in front of the front side of the panel, and a loading position wherein the pressure plate is pivoted to a position generally laterally away from front side of the panel. Most preferably, the operating position and loading position of the cross arm are reversed when the adjustable mounting means is switched between being mounted adjacent one side edge of the panel to the other side edge of the panel.

In a fourth aspect of the invention, a volume controlling apparatus generally comprises a panel, a pressure plate, and adjustable mounting means for movably mounting the pressure plate on the panel so that the flexible venous reservoir can be positioned between the panel and the pressure plate and in contact with both to adjustably limit the maximum volume of the flexible venous reservoir. A dial indicator is operatively connected to the adjustable mounting means so that the dial indicator rotates as the pressure plate is moved relative to the panel. The dial indicator is marked with indicia corresponding to the approximate maximum volume permitted in the flexible venous reservoir for various positions of the pressure plate relative to the panel.

Alternatively, the dial indicator is operatively connected to the adjustable mounting means via a cable linkage. A suitable drive means may also be provided for driving the cable linkage to drive the adjustable mounting means to move the pressure plate relative to the panel.

Preferably, the dial indicator includes indicia along at least two scales corresponding to at least two flexible venous reservoirs having blood storage chambers of different sizes.

These and other features will be pointed out below.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
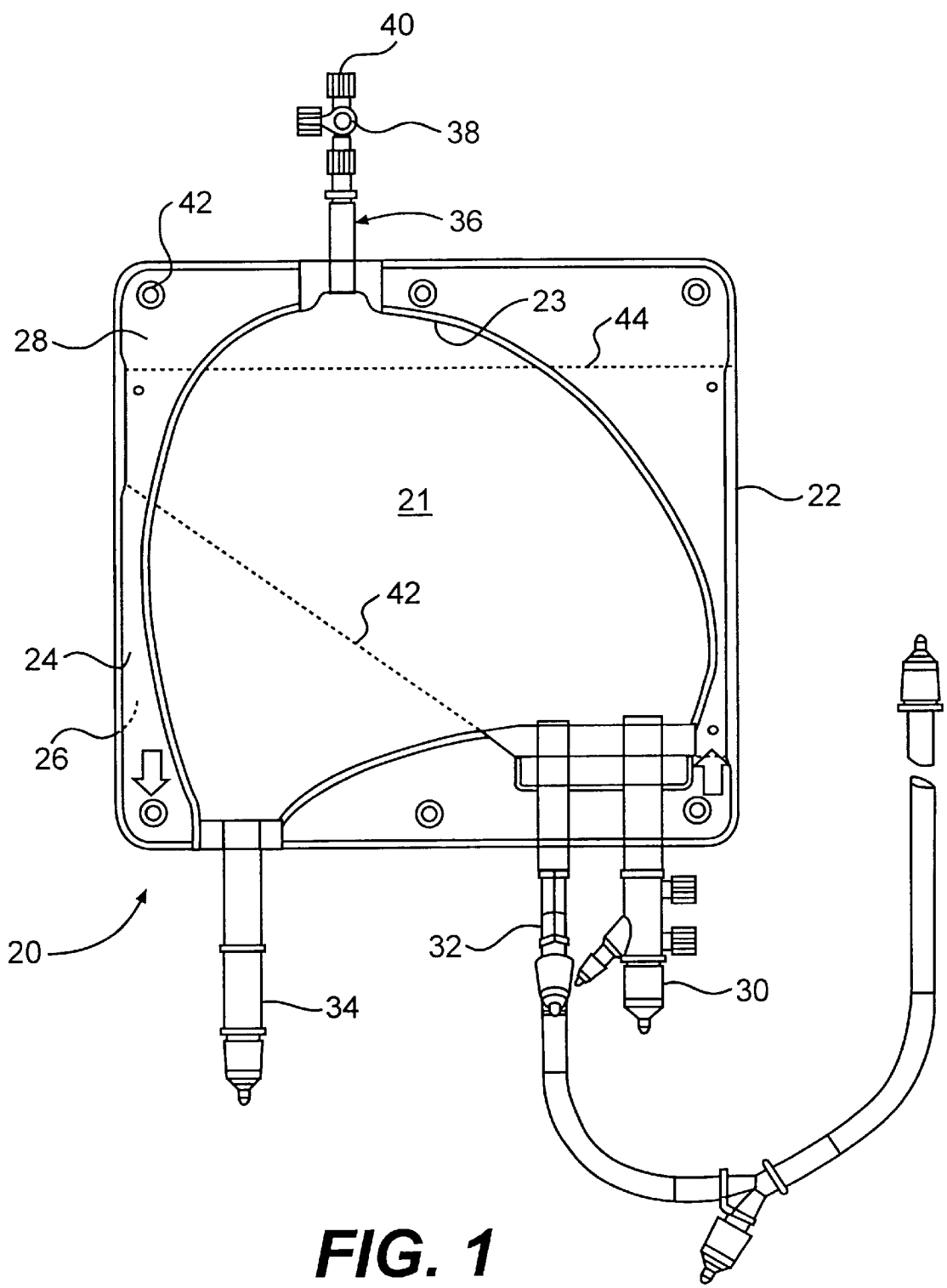
FIG. 1 is a front plan view of a flexible venous reservoir of the type which could be used in connection with the invention.

Referring now to FIG. 1, a front plan view of a flexible venous reservoir 20 is illustrated. The body 22 of the flexible venous reservoir 20 is conveniently fabricated from two sheets of flexible, substantially transparent, polymeric material forming a first (front in this view) 24 and a second (rear in this view) wall 26, the first and second walls being heat sealed in a region 28 adjacent to their edges to form a bag-like construction.

Conveniently, the flexible venous reservoir 20 is provided with two inlets 30 and 32, one to serve to inlet blood coming directly from the patient's circulation, and the other to serve to inlet cardiotomy blood. An outlet 34 is provided to conduct the blood to the next stage of processing. A specialized air vent 36 is provided at the top of the flexible venous reservoir 22 so that the air from bubbles that have separated from blood can be purged. The vent 36 conveniently includes a valve 38 and a luer connection 40.

The flexible venous reservoir 20 defines an internal blood storage chamber 21 formed by sheets of polymeric material and heat seals. The upper perimeter 23 of the blood storage chamber 21 is preferably generally arcuate to define a generally arcuate blood flow path or passage through the blood storage chamber 21 between the inlets 30, 32 and outlet 34. The vent 36 preferably communicates with the top of the arc of the blood storage chamber 21, as illustrated in FIG. 1.

A series of holes 42 within the heat-sealed region 28 may conveniently be used to support the reservoir 20. A screen 43, formed of a fine mesh of polymeric material and disposed within the bag-like construction flexible venous reservoir 20, receives the blood entering through both inlets 30 and 34. Under most operating conditions, all of the blood must pass through the screen 42 to reach the outlet 34, but the upper margin 44 of the screen is left open as a bypass route for the blood to the outlet in unusual conditions.

Figure 2:
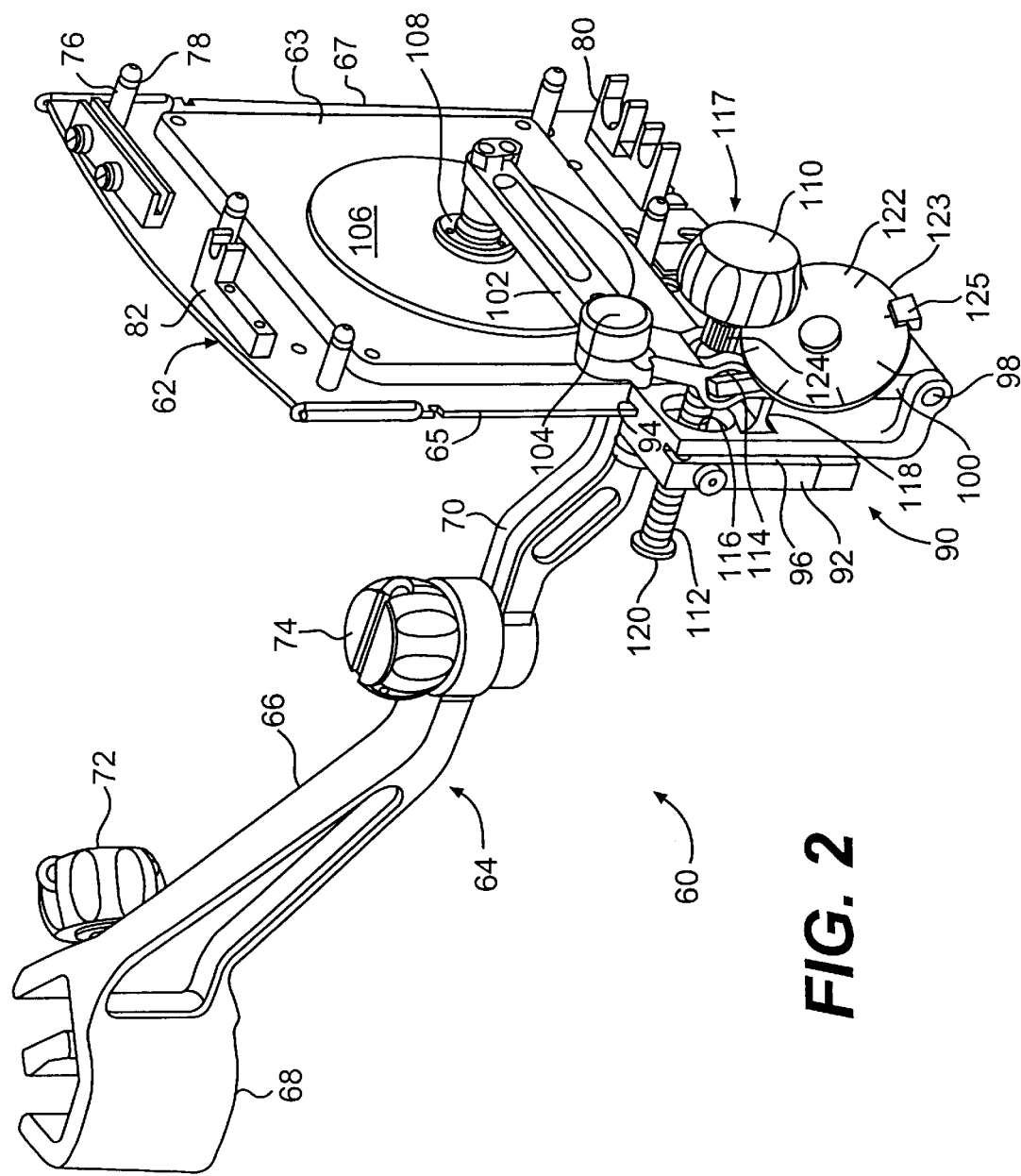
FIG. 2 is a perspective view of a preferred embodiment of a volume controlling support adapted to receive, for example, the flexible venous reservoir of FIG. 1.

Referring now to FIG. 2, a perspective view of a volume controlling support 60 according to the present invention is illustrated. The support 60 includes a panel 62 which serves as a backstop against which the flexible venous reservoir 20 can be compressed. The panel 62 is conveniently attached to a mounting arm 64 which includes first arm section 66 having a mounting clamp 68, and a second arm section 70 attached to panel 62. The mounting clamp 68 can be tightened onto a pole or other stand in the operating theater by turning clamp tightening knob 72, and the angular relation between first arm section 66 and second arm section 70 can be adjusted by turning arm tightening knob 74.

A series of pins 76, each having a circumferential groove 78 are attached to panel 62, positioned so that the pins 76 can enter the holes 42 in the reservoir 20, with the reservoir hanging in the grooves. Other expedients, such as spring loaded clips, will suggest themselves to the artisan for securing the reservoir 20 to the panel 62.

An inlet clamp 80 is preferably provided, which is sized and shaped to receive the inlets 30 and 32, conveniently with a snap fit. A vent clamp 82 is preferably provided to receive the reservoir's vent 36, and an outlet clamp 84 (seen in FIGS. 4 and 5) is preferably provided to receive the reservoir's outlet 34.

Figure 4A:
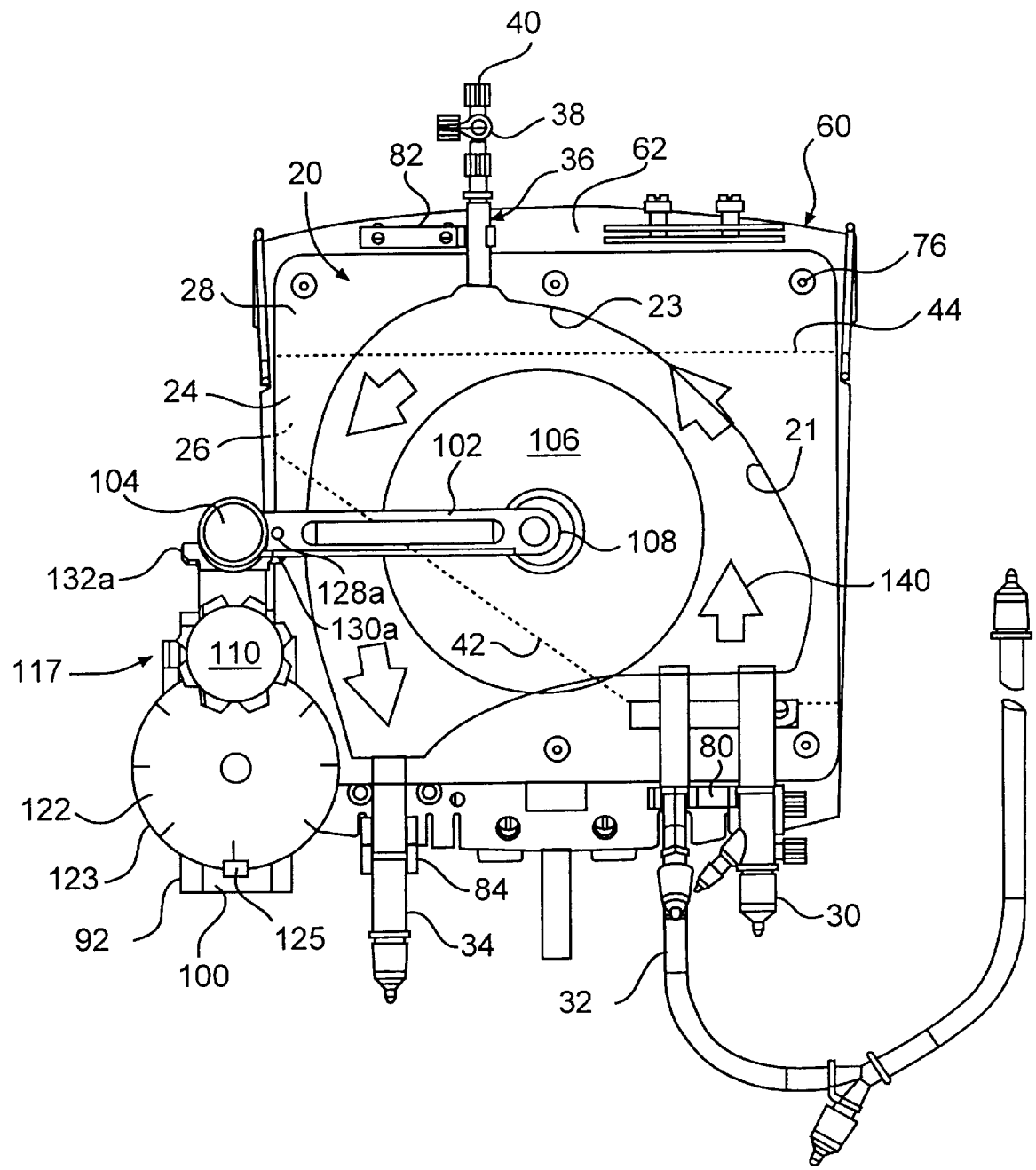
FIG. 4a is a perspective view of the volume controlling support with a flexible venous reservoir in place, particularly illustrating a flow path above the pressure plate.
Figure 4B:
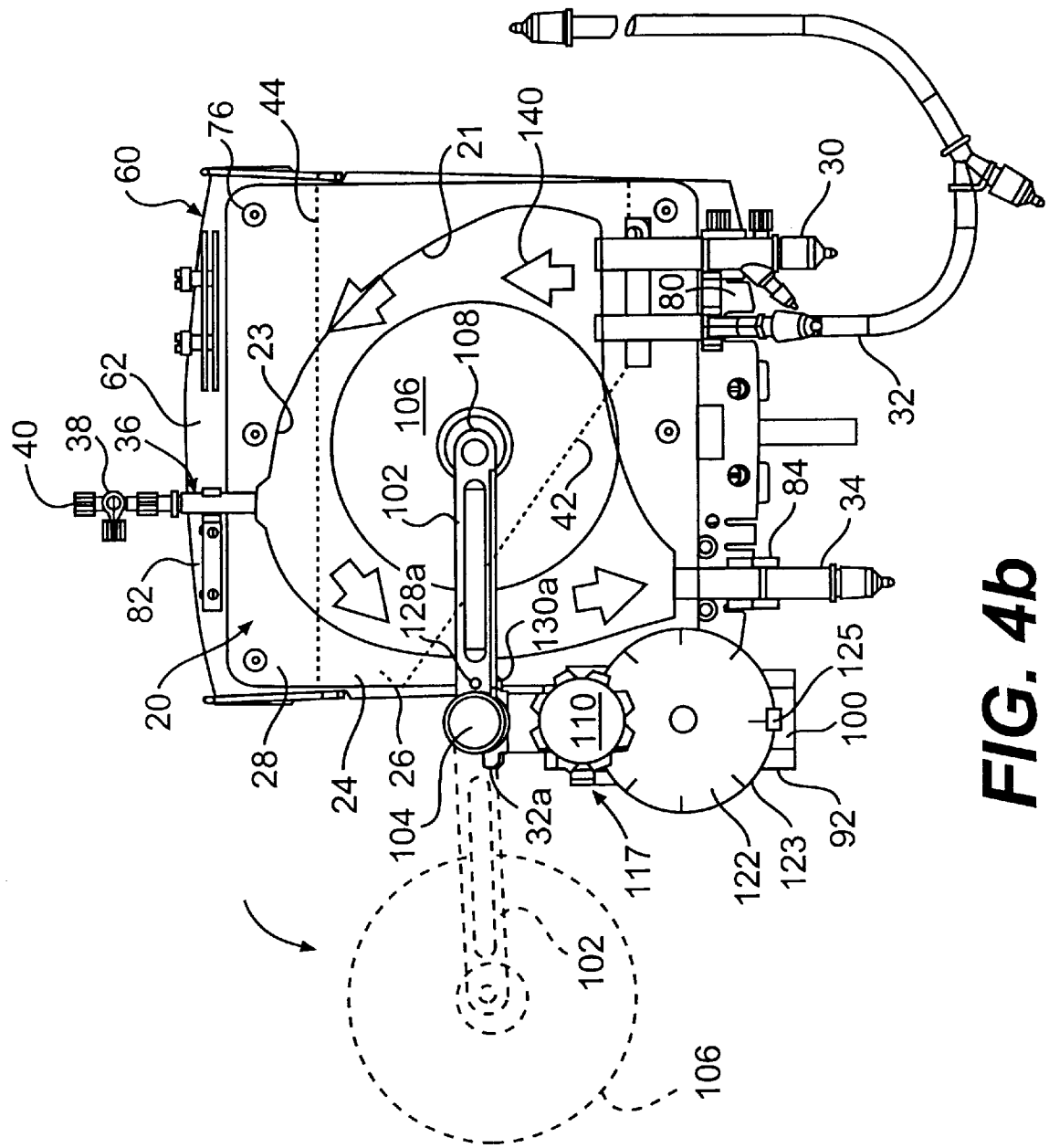
FIG. 4b is similar to FIG. 4a except that it shows a cross arm and pressure plate in phantom in a positioned pivoted laterally away from the panel and flexible venous reservoir.

The panel 62 has a front side (the reservoir side in FIGS. 2, 4a, 4b and 5), and the direction between the opposite side edges 65 and 67 of the panel 62 constitutes a lateral direction (e.g., rightwardly or leftwardly away from the panel in FIGS. 4a and 4b). The directions perpendicular to the plane of the panel 62 constitute either the forward or rearward direction, it being understood that the direction upwardly out of the page of FIGS. 4a and 4b constitutes the forward direction.

The panel 62 preferably includes a flat transparent window 63 that supports the back side of the flexible venous reservoir. The panel, however, may alternatively be formed by any suitable support structure, such a grill, grid or mesh, solid opaque or translucent surface, etc.

Various details of a preferred flexible venous reservoir 20 and preferred backstop panel 62 are also disclosed in our co-pending, co-assigned U.S. patent application Ser. No. 08/966,399, filed Nov. 7, 1997, on Reservoir Mounting Bracket, which is incorporated herein by reference.

A volume limit assembly 90 acts to limit the maximum volume the flexible venous reservoir 20 can contain. The volume limit assembly 90 includes a mounting frame 92 which as a pair of grooves 94 and 96; each of these grooves is sized to receive panel 62 within itself so that the volume limit assembly 90 can be clamped to the left or to the right edge of panel 62. In the present illustration, the mounting frame 92 is depicted clamped to the left edge of panel 62, with the panel 62 in groove 94. The volume controlling support can thus easily be set up for right-handed or left-handed operation depending on the preference of the perfusionist.

The mounting frame 92 is pivotally mounted at a pivot joint 98 to a lever 100. The lever 100 is pivotally attached at its other end to a cross arm 102 at pivot 104. The mounting frame 92 constitutes a preferred embodiment of a first arm (also 92), and the lever 100 constitute a preferred embodiment of a second arm (also 100). It will be appreciated that the first and second arms 92 and 100 could be modified so that the first arm 92 pivots relative to the panel 62, and the second arm either also pivots or is connected so as to merely move outwardly with little or no pivotable motion of the second arm relative to the panel.

As used herein, motion, such as pivoting, one member relative to another means that either member can be viewed as stationary outside the system comprising the two members so long as one of the members moves relative to the other.

The cross arm 102 is preferably attached to a pressure plate 106 in such a manner as to allow the pressure plate 106 to articulate, conveniently by a ball-and-socket joint 108, thus permitting the pressure plate 106 to be self-leveling against the flexible venous reservoir 20. Most conveniently, the ball-and-socket joint 108 has a resilient socket so that the pressure plate 106 can be rapidly replaced with another of a different size or shape to accommodate alternative flexible venous reservoirs 20. Alternative means for connecting the pressure plate 106 to the cross arm 102 to allow articulation of the pressure plate 106 include, for example, a universal joint, flexible rubber connection, etc.

Figure 4C:
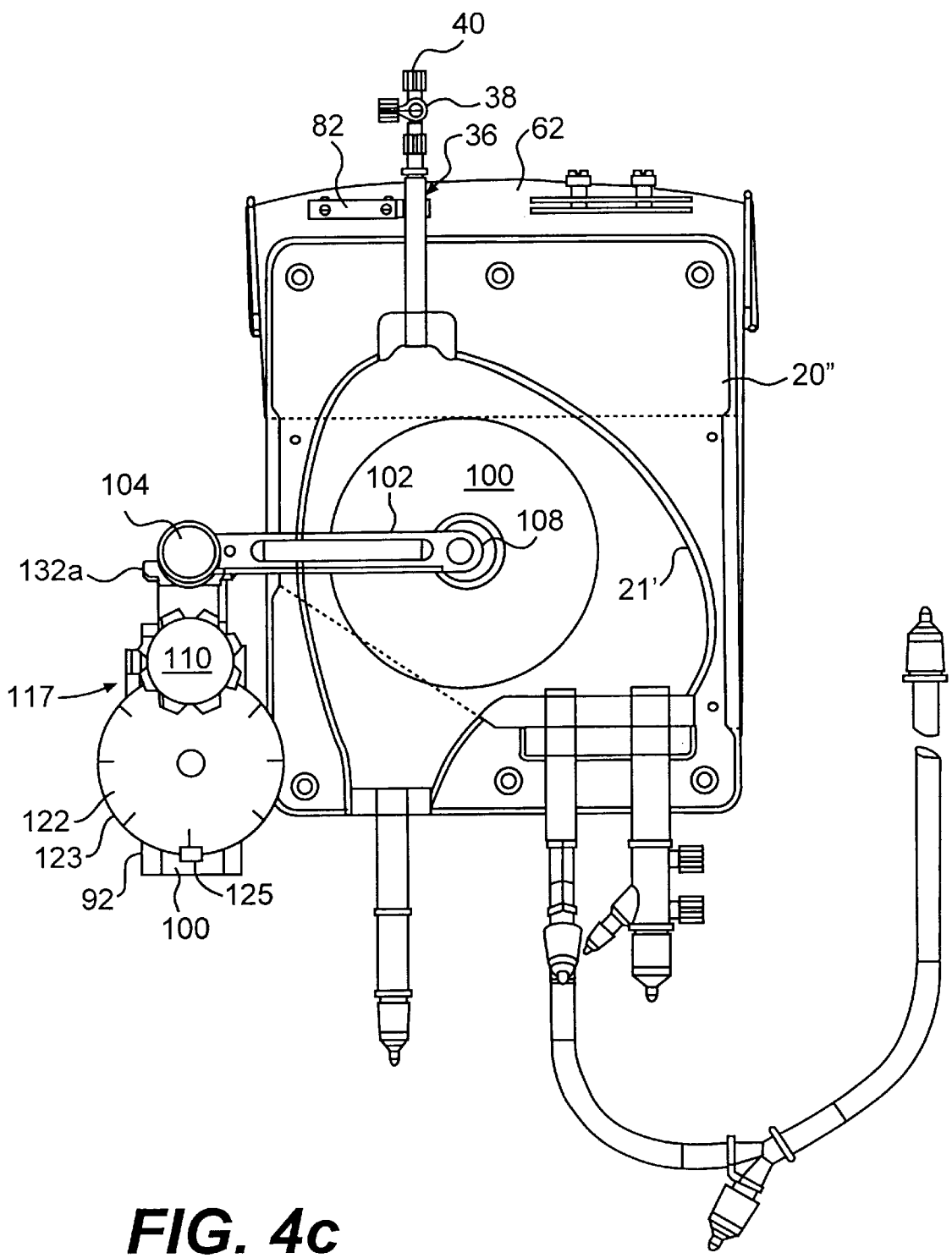
FIG. 4c is a perspective view of the volume controlling support with a second flexible venous reservoir in place.

Most preferably, at least two sizes of flexible venous reservoirs 20 and pressure plates 106 are provided. As illustrated in FIG. 4c, these include a second flexible venous reservoir 20' forming a different size blood storage chamber 21' than the blood storage chamber 21 of the first flexible venous reservoir 20, and a second pressure plate 106' of different size than the first pressure plate 106 to correspond to the size of the blood storage chamber of the second flexible venous reservoir. The first and second reservoirs and pressure plates may otherwise be of the same design, although it is contemplated that they could otherwise have different configurations, be formed of different materials or constructions. The ball-and-socket joint 108 or other suitable mounting means in this embodiment would releasably hold the pressure plate 106 on the cross arm 102 to permit interchanging the first and second pressure plates. Additional types of sizes of pressure plates could also be provided.

Most preferably, the pressure plate 106 is generally flat, circular and is formed of transparent polymeric material.

Alternatively, the pressure plate may be formed in other configurations, and may comprise a grill, grid or mesh, solid opaque plate or other construction, although these are not preferred.

The preferred circular configuration of the pressure plate 106 and the preferred size of the pressure plate 106 help define the blood flow passage through the blood storage chamber 21 of the venous reservoir 20 as generally arcuate between the circular periphery of the pressure plate 106 and the generally arcuate upper periphery of the blood storage chamber 21. This provides access to this part of the venous reservoir 20, as well as providing this arcuate flow channel or passage when the pressure plate 106 is moved to a position closest to the panel 62 as permitted by the stop bar 118. The gap between the pressure plate 106 and the panel 62 is very narrow at this position (which may be referred to as a "closed position" notwithstanding the fact that the blood flow channel or passage is open and the fact that blood flow is preferably not completely closed off through the blood storage chamber 21 behind the pressure plate 106).

In one embodiment, the blood flow channel or passage between the periphery of the pressure plate 106 and the upper periphery 23 of the blood storage chamber 21 may have a greater cross sectional area generally adjacent the vent 36 so that blood tends to decelerate adjacent the vent 36 to assist in allowing any air emboli entrained in the blood flow to travel upwardly to the vent 36.

It will also be appreciated that the pressure plate 106 in its closed position and the arcuate blood flow passage can be employed to facilitate in the priming or draining of the blood storage chamber 21.

Also, preferably, one side of the blood storage chamber 21 is substantially covered by the pressure plate 106 other than the blood flow passage along the upper periphery of the blood storage chamber, and the panel 62 substantially covering the other side of the blood storage chamber 21, at least other than the blood flow passage. Most preferably, the transparent window 63 of the preferred embodiment of the panel 62 completely covers the "back" side of the blood storage chamber 21 of the venous reservoir 20.

The position of lever 100 around pivot joint 98 can be adjusted by turning volume control knob 110. Turning volume control knob 110 rotates lead screw 112, which interacts with a pivoting trunion 114 in lever 100, and with threaded fitting 116 within the frame 92 (which may also be a pivotable trunion). The lead screw 112, and conveniently its volume control knob 110, constitute an operative part of a preferred embodiment of a position regulating apparatus 117. The maximum travel of lead screw 112 is limited at one end by stop bar 118, and at the other end by screw stop 120.

The stop bar 118 defines the limit to the range of motion of the pressure plate 106 that is referred to as the "closed" position, and the screw stop 120 defines the limit of the range of motion of the pressure plate that is referred to as the "open" position. Most preferably, the open position is sufficiently open to permit the cross arm 102 to be pivoted laterally from its operating position (solid in FIG. 4b) to its loading position (phantom in FIG. 4b) even when the venous reservoir is full. Most preferably, the "closed" position does not completely close the covered portion of the blood storage chamber to blood flow.

Preferably, a dial indicator 122 has teeth at its periphery 123 which intermesh with teeth on a pinion gear 124 on lead screw 112 such that the dial indicator rotates in proportion to the rotation of the lead screw 112, calibrated to provide an approximate read-out of the maximum volume which that positioning of the cross arm 102 and pressure plate 106 permits within the flexible venous reservoir 20.

Most preferably, the gear ratio between the pinion gear 124 and the dial indicator 122 is such that the full range of motion of the lead screw 112, cross arm 102 and pressure plate 106 causes less than a full rotation of the dial indicator 122, most preferably just slightly less than full rotation. For example, the lead screw may advance one inch (25.4 mm) over four rotations, and the gear ratio (teeth ratio) between the pinion gear 124 and the dial indicator may be approximately 13:93. The range of motion can then be set to provide less than one full rotation of the dial indicator 122.

Figure 6:
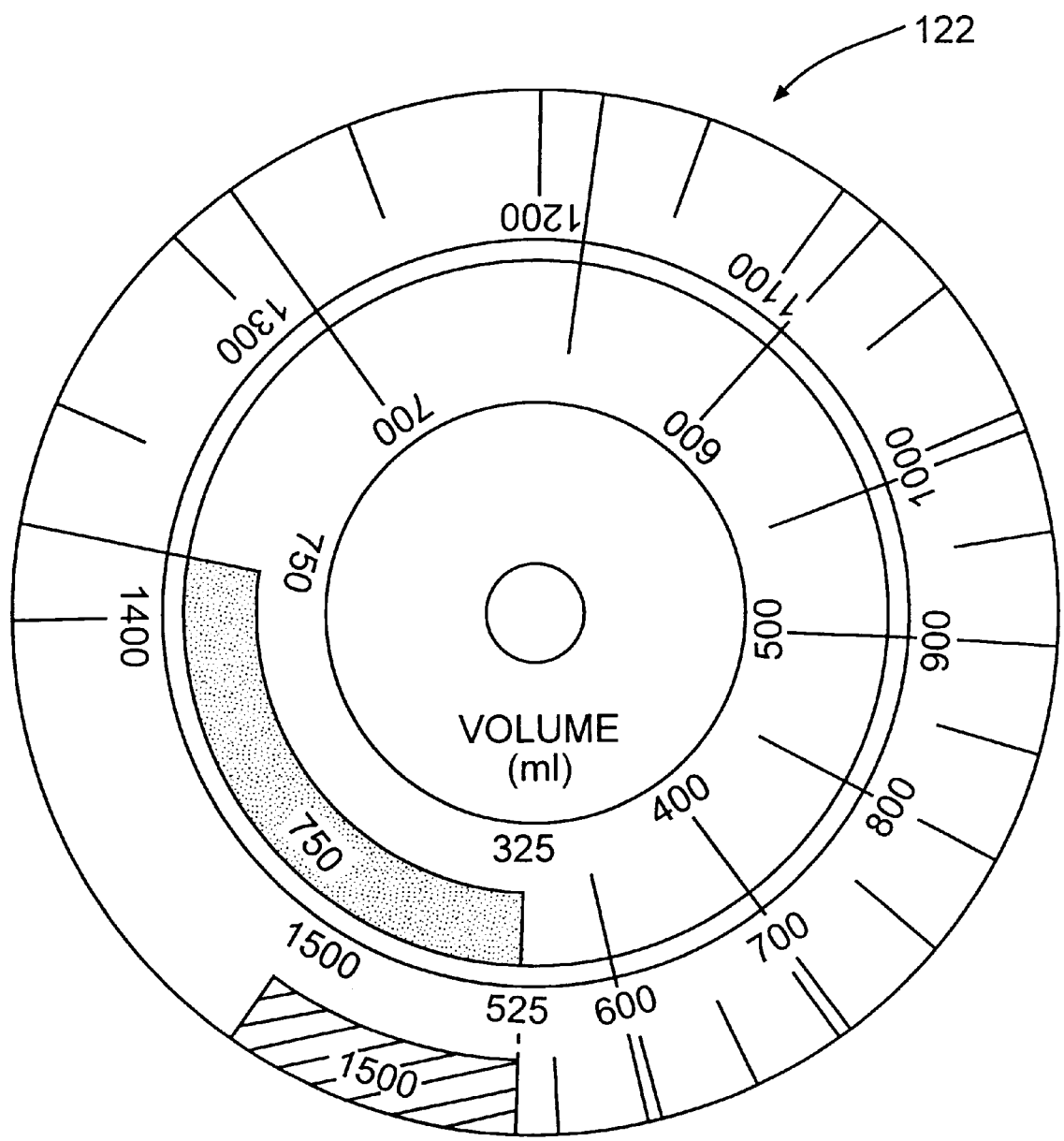
FIG. 6 is a front plan view of a preferred dial indicator.

Dial indicator 122 is provided with indicia which are read in reference to pointer 125. Conveniently, the indicia may indicated several scales which are calibrated to different sizes and models of flexible venous reservoirs 20. For example, two scales may be provided as illustrated in FIG. 6. The dial indicator 122 may also be considered as a portion of position regulating apparatus 117.

The dial indicator 122 is believed to provide a high degree of resolution within a relatively small area. This is because the indicia are provided circumferentially along the dial indicator 122, resulting in indicia along an circle having a circumference equal to $\pi$ times the diameter of the indicia. A longitudinal volume indicator, in contrast, would require a length more than three times longer than the diameter of the indicia to provide the same amount of resolution.

The cross arm 102 is preferably pivotable generally laterally between an operating position (solid lines in FIGS. 4a and 4b) and a loading position (phantom lines in FIG. 4b). In the operating position, the pressure plate 106 is held in front of the front side of the panel 62 to restrain the flexible venous reservoir 20 between the pressure plate 106 and panel 62. In the loading position, the pressure plate 106 is pivoted to a position generally laterally away from front side of the panel 62 to load or unload the flexible venous reservoir 20 or otherwise obtain greater access to the flexible venous reservoir 20. The operating position and loading position of the cross arm 106 are reversed when the adjustable mounting means is switched between being mounted adjacent one side edge of the panel 62 (e.g., the left side edge in FIG. 4) to the other side edge of the panel 62 (e.g., the right side edge).

Figure 3:
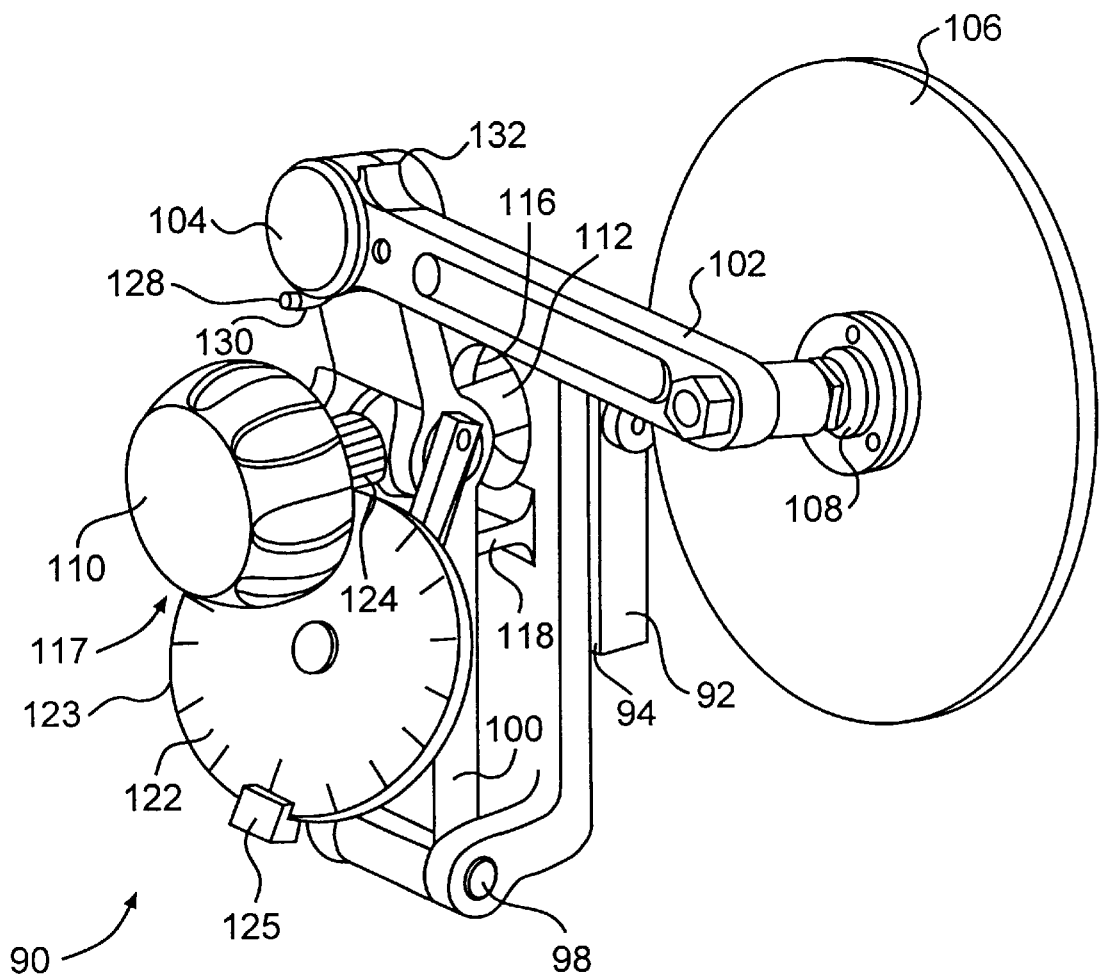
FIG. 3 is a detail perspective view of the volume limit assembly of the volume controlling support of FIG. 2.

Referring now to FIG. 3, a detail perspective view of the volume limit assembly 90 of the volume controlling support 60 is illustrated. In this view a rotation stop 128 can be appreciated, which stop interacts with projecting ears 130 and 132. The cross-arm 102 can pivot from a first position defined by the contact with rotation stop 128 and projecting ear 130 for left-handed operation when the volume limit assembly is attached to the left side of panel 62 (the position illustrated in solid lines in FIG. 4b), to a second position defined by the contact with rotation stop 128 and projecting ear 132 for right-handed operation when the volume limit assembly is attached to the right side of panel 62. This arrangement conveniently allows the pressure plate 106 to be rotated completely out of the way of the flexible venous reservoir 20 (as illustrated in phantom in FIG. 4b) if for any reason the perfusionist wishes complete access to the reservoir.

Referring now to FIGS. 4a and 4b, is a perspective view of the volume controlling support 60 with a flexible venous reservoir 20 in place is illustrated. It is particularly to be noted that the pressure plate 106 is shaped and sized so that a significant flow passage (depicted by the sequence of arrows 140) exists within the flexible venous reservoir 20 from the inlet 30 to the outlet 34 adjacent to portions of the flexible venous reservoir which are pot covered by the pressure plate. As used herein, the phrase "significant flow passage" means that the flow passage is sufficient to allow various flow rates that would be expected during cardiopulmonary bypass. This also allows the flexible venous reservoir 20 to be inspected and manipulated to enhance the clearance of air bubbles from the blood contained in the flexible venous reservoir without releasing the reservoir from the volume limiting restraint provided by the pressure plate 106.

In FIGS. 4a and 4b, one preferred way of providing rotational limits for the cross arm 102 is provided. In this preferred embodiment, rotation stop 128a is positioned on the cross arm 102, and projecting ears 130a and 132a are provided on lever 100. Any other suitable methods or structures that provide rotational limits may also be employed.

As used herein, the phrase "adjustable mounting means for movably mounting the pressure plate on the panel so that the flexible venous reservoir can be positioned between the panel and the pressure plate and in contact with both to adjustably limit the maximum volume of the flexible venous reservoir" includes the preferred embodiment for accomplishing this function, e.g., the cross arm 102, lead screw 112, frame 92, lever 100 and knob 110, as well as any other way to accomplishing this function. For example, adjustable mounting means is also intended to cover the types of mechanisms disclosed in U.S. Pat. Nos. 5,352,218; 5,573,526; 5,693,039 and 5,720,741, which are incorporated herein by reference.

When the phrase, "attachable to the panel adjacent either side edge of the panel" is added to the adjustable mounting means expression, any suitable means for mounting an assembly on along either side edge of a panel may be employed, for example, threaded fasteners, snap connections, magnetic means (possibly in combination with other means), overcenter locking or clamping mechanisms (such as provided by vices that would either clamp the adjustable mounting means to the panel or the panel to the adjustable mounting means) or any combination of such means. Most preferably, the adjustable mounting means is releasably "attachable to the panel adjacent either side edge of the panel" by the pair of grooves 94 and 96 that alternatively receive the panel 62 depending upon whether the frame 92 is being mounted on the left or right side edge of the panel 62, and the frame 92 is clamped to the panel 62.

Figure 5:
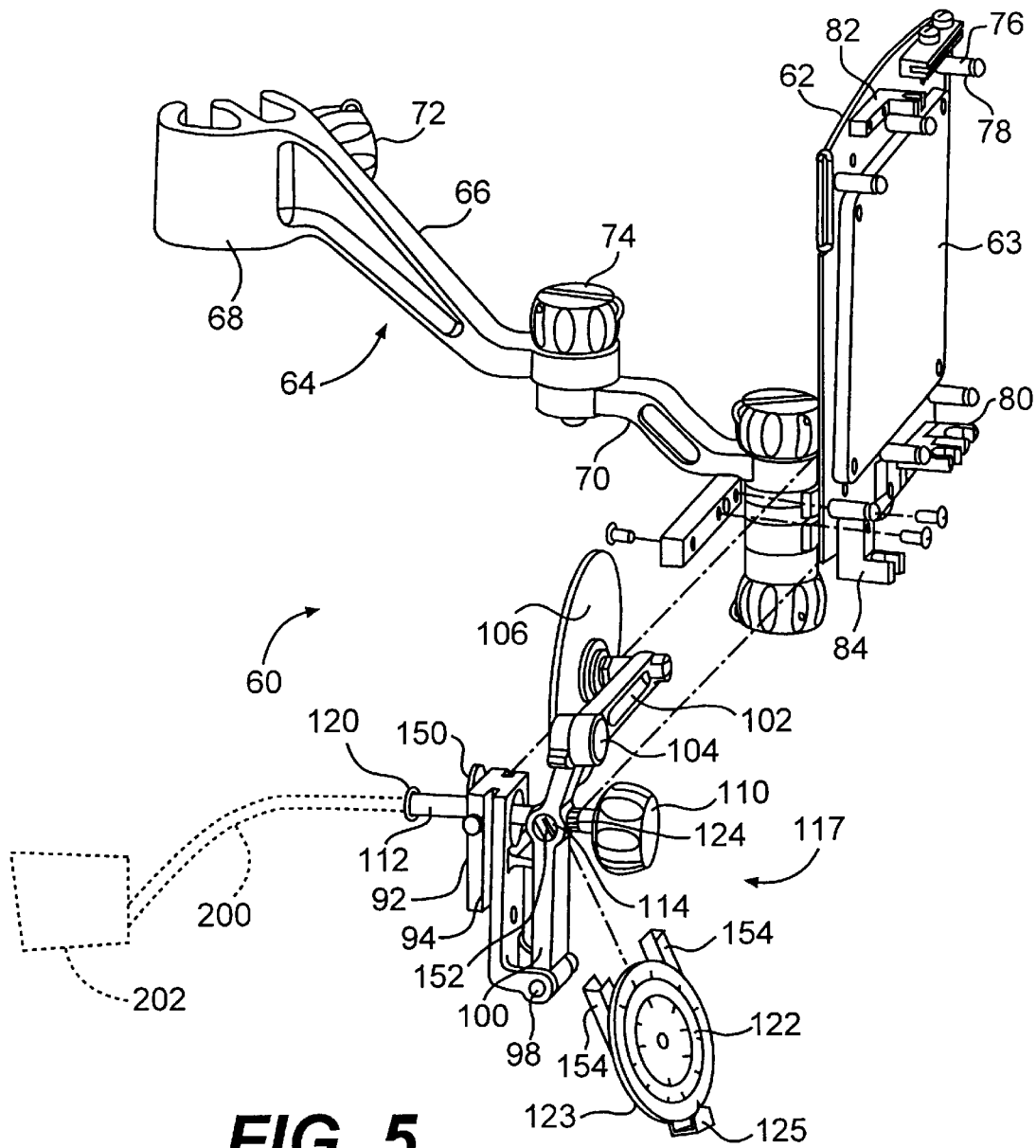
FIG. 5 is an exploded view of the volume controlling support particularly illustrating a preferred mode for attaching the dial indicator to the rest of the volume limit assembly.

Referring now to FIG. 5, an exploded view of the volume controlling support 60 is illustrated. In this view it can be more readily appreciated that e.g. one or more thumbscrews 150 can be provided to conveniently attach the volume limit assembly 90 to the panel 62. It can also be seen that the trunion 114 may have projecting tabs 152 extending on each side (only one can be seen the this view, the other being on the far side of the volume limit assembly 90). Conveniently, these engage complementary rails 154 attached to the dial indicator 122 so as to guide and support the dial indicator and cause its threaded periphery 123 to engage the pinion gear 124. Conveniently, a bolt or allen screw can be used to attach each of the rails 154 to the projecting tabs 152. It will be understood that the projecting tabs 152 and complementary rails 154 constitute a preferred embodiment of a key-and-slot connection. Another example is to reverse the tabs and rails. Any other suitable methods of connecting the dial frame (also 154) to the ends of the trunion 114 may be employed.

An alternative linkage of the a volume or position indicator and/or drive motor is illustrated schematically in phantom in FIG. 5. This alternative linkage comprises a cable linkage 200 and a means 202 for driving the cable linkage or indicating the maximum volume of the blood storage chamber 21 or position of the pressure plate 62. The cable linkage 200 of this alternative would be connected to the back end of the lead screw 112 so that the cable 200 turns as the lead screw 112 turns. The means 202 could merely be an dial indicator similar in some respects to the dial indicator 122 mounted at another location, for example, at the discretion of the perfusionist, a drive motor, and/or an electromechanical linkage with a computer or display. Of course, other position sensors or drive means could alternatively be employed, and further intermediate linkages could be provided, such as intermeshing gears.

The dial indicator 122 can readily be recalibrated if it is reattached to the apparatus. A preferred way to accomplish recalibration is to first move the pressure plate 106 to its closed position (i.e., smallest gap between the pressure plate 106 and panel 62). The dial indicator 122 is then reinstalled with its orientation being such that its minimum volume indicia is aligned with the pointer 125. This accomplishes the recalibration. There is no need to recalibrate the dial indicator 122 unless it is removed from the apparatus.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A combination of a flexible venous reservoir and a volume controlling apparatus, the flexible reservoir comprising flexible walls defining a blood storage chamber having an upper perimeter and a lower perimeter, and an inlet and an outlet to the blood storage chamber arranged on the lower perimeter and defining a blood flow path through the blood storage chamber, the volume controlling apparatus comprising:

a panel, a pressure plate having an exterior perimeter and adjustable mounting means for movably mounting the pressure plate on the panel so that the flexible venous reservoir can be positioned between the panel and the pressure plate and in contact with both to adjustably limit the maximum volume of the flexible venous reservoir;

the pressure plate being sized relative to the blood storage chamber such that a significant blood flow passage is defined from the inlet, upwardly around a portion of the exterior perimeter of the pressure plate towards the upper perimeter of the blood storage chamber, and downwardly around a further portion of the exterior perimeter of the pressure plate to the outlet.

2. The combination according to claim 1 wherein the adjustable mounting means comprises:

a cross arm having one end connected to the pressure plate; and a position regulating apparatus for moving the cross arm relative to the panel and holding the cross arm in position.

3. The combination according to claim 2 wherein the position regulating apparatus comprises:

first and second arms pivotably connected together at one end of each of the first and second arms, the first arm being mounted to the panel and the second arm being mounted to the cross arm;

a lead screw engaging the first and second arms to pivot the second arm relative to the first arm as the lead screw is turned to move the cross arm and pressure plate relative to the panel.

4. The combination according to claim 3 wherein the pressure plate is free to articulate relative to the cross arm.

5. The combination according to claim 4 wherein the pressure plate is mounted to the cross arm by a ball-and-socket joint.

6. The combination according to claim 3 wherein the position regulating apparatus further comprises:

a knob connected to the lead screw for manually turning the lead screw; and a dial indicator connected to the lead screw so that the dial indicator rotates as the lead screw is turned, the dial indicator being marked with indicia corresponding to the approximate maximum volume permitted in the flexible venous reservoir for various positions of the pressure plate relative to the panel.

7. The combination according to claim 6 wherein the position regulating apparatus further includes stops that limit the range of motion of the second arm relative to the first arm, the dial indicator rotating through no more than one full rotation throughout the range of motion of the second arm relative to the first arm.

8. The combination according to claim 6 wherein the lead screw engages the second arm via a trunion that is pivotably mounted to the second arm so that the trunion maintains a constant orientation relative to the first arm as the lead screw is turned, the dial indicator being mounted to the trunion so that the dial indicator maintains a constant orientation relative to the first arm and panel as the second arm pivots relative to the first arm.

9. The combination according to claim 8 further comprising a dial frame for the indicator dial and a key-and-slot connection between dial frame and trunion to mount the indicator dial on the trunion.

10. The combination according to claim 8 wherein:

the first arm comprises a frame mountable in fixed relationship with the panel, the frame including two hub portions each having a through opening;

the second arm constitutes a lever having first and second ends; and the position regulating apparatus further comprising an axle through the lever and the through openings of the mounting frame to pivotably mount the first end of the lever on the mounting frame;

the cross arm being connected to the second end of the lever, and the trunion being mounted in the lever intermediate the first and second ends thereof.

11. The combination according to claim 1 wherein the flexible venous reservoir further includes a vent passageway into the blood storage chamber generally adjacent the upper perimeter of the blood storage chamber for venting air bubbles from the blood storage chamber, the pressure plate being generally flat and having a generally circular configuration to define the blood flow passage as generally arcuate.

12. The combination according to claim 11 wherein one side of the blood storage chamber is substantially covered by the pressure plate other than the blood flow passage along the upper periphery of the blood storage chamber, the panel substantially covering the other side of the blood storage chamber at least other than the blood flow passage.

13. The combination according to claim 12 wherein the pressure plate is formed of transparent material.

14. The combination according to claim 1 wherein the flexible venous reservoir and pressure plate constitute a first flexible venous reservoir and a first pressure plate, respectively, the combination further comprising:

a second flexible venous reservoir forming a different size blood storage chamber than the blood storage chamber of the first flexible venous reservoir; and a second pressure plate of different size than the first pressure plate to correspond to the size of the blood storage chamber of the second flexible venous reservoir;

the first and second pressure plates being interchangeably mountable by the adjustable mounting means.

15. Volume controlling apparatus for a flexible venous reservoir having flexible walls defining a blood storage chamber and an inlet and an outlet to the blood storage chamber defining a blood flow path through the blood storage chamber between the inlet and outlet, the volume controlling apparatus comprising:

a panel, a pressure plate; and adjustable mounting means for movably mounting the pressure plate on the panel so that the flexible venous reservoir can be positioned between the panel and the pressure plate and in contact with both to adjustably limit the maximum volume of the flexible venous reservoir;

the pressure plate being free to articulate relative to the adjustable mounting means to allow the pressure plate to self-level with respect to the flexible venous reservoir.

16. The apparatus according to claim 15 wherein the adjustable mounting means comprises:

a cross arm having one end connected to the pressure plate; and a position regulating apparatus for moving the cross arm relative to the panel and holding the cross arm in position.

17. The apparatus according to claim 16 wherein the position regulating apparatus comprises:

first and second arms pivotably connected together at one end of each of the first and second arms, the first arm being mounted to the panel and the second arm being mounted to the cross arm;

a lead screw engaging the first and second arms to pivot the second arm relative to the first arm as the lead screw is turned to move the cross arm and pressure plate relative to the panel.

18. The apparatus according to claim 17 wherein the pressure plate is mounted to the cross arm by a ball-and-socket joint.

19. The apparatus according to claim 17 wherein the position regulating apparatus further comprises a dial indicator connected to the lead screw so that the dial indicator rotates as the lead screw is turned, the dial indicator being marked with indicia corresponding to the approximate maximum volume permitted in the flexible venous reservoir for various positions of the pressure plate relative to the panel.

20. The apparatus according to claim 19 wherein the position regulating apparatus further includes stops that limit the range of motion of the second arm relative to the first arm, the dial indicator rotating through no more than one full rotation throughout the range of motion of the second arm relative to the first arm.

21. The apparatus according to claim 18 wherein the lead screw engages the second arm via a trunion that is pivotably mounted to the second arm so that the trunion maintains a constant orientation relative to the first arm as the lead screw is turned, the dial indicator being mounted to the trunion so that the dial indicator maintains a constant orientation relative to the first arm and panel as the second arm pivots relative to the first arm.

22. The apparatus according to claim 15 wherein the pressure plate is generally flat and has a generally circular configuration.

23. The apparatus according to claim 22 wherein the pressure plate is formed of transparent material.

24. A combination comprising:
a volume controlling apparatus according to claim 15; and
a flexible venous reservoir comprising flexible walls defining a blood storage chamber, and an inlet and an outlet to the blood storage chamber defining a blood flow path through the blood storage chamber between the inlet and outlet.

25. Volume controlling apparatus for a flexible venous reservoir having flexible walls defining a blood storage chamber and an inlet and an outlet to the blood storage chamber defining a blood flow path through the blood storage chamber between the inlet and outlet, the volume controlling apparatus comprising:
a panel having opposite side edges;
a pressure plate; and
adjustable mounting means, attachable to the panel adjacent either side edge of the panel, for movably mounting the pressure plate on the panel so that the flexible venous reservoir can be positioned between the panel and the pressure plate and in contact with both to adjustably limit the maximum volume of the flexible venous reservoir, the adjustable mounting means comprising:
a cross arm having one end connected to the pressure plate; and
a position regulating apparatus for moving the cross arm relative to the panel and holding the cross arm in position.

26. The apparatus according to claim 25 wherein the panel has a front side and the direction between the opposite side edges of the panel constitutes a lateral direction, the cross arm being pivotable generally laterally between:
an operating position wherein the pressure plate is held in front of the front side of the panel; and
a loading position wherein the pressure plate is pivoted to a position generally laterally away from front side of the panel.

27. The apparatus according to claim 26 wherein the operating position and loading position of the cross arm are reversed when the adjustable mounting means is switched between being mounted adjacent one side edge of the panel to the other side edge of the panel.

28. The apparatus according to claim 27 wherein the pressure plate is free to articulate relative to the cross arm.

29. The apparatus according to claim 28 wherein the pressure plate is mounted to the cross arm by a ball-and-socket joint.

30. The apparatus according to claim 27 wherein the pressure plate is generally flat, has a generally circular configuration, and is formed of transparent material.

31. The apparatus according to claim 27 wherein the position regulating apparatus comprises:
first and second arms pivotably connected together at one end of each of the first and second arms, the first arm being mounted to the panel and the second arm being mounted to the cross arm;
a lead screw engaging the first and second arms to pivot the second arm relative to the first arm as the lead screw is turned to move the cross arm and pressure plate relative to the panel.

32. The apparatus according to claim 31 wherein the position regulating apparatus further comprises a dial indicator connected to the lead screw so that the dial indicator rotates as the lead screw is turned, the dial indicator being marked with indicia corresponding to the approximate maximum volume permitted in the flexible venous reservoir for various positions of the pressure plate relative to the panel.

33. The apparatus according to claim 32 wherein the lead screw engages the second arm via a trunion that is pivotably mounted to the second arm so that the trunion maintains a constant orientation relative to the first arm as the lead screw is turned, the dial indicator being mounted to the trunion so that the dial indicator maintains a constant orientation relative to the first arm and panel as the second arm pivots relative to the first arm.

34. The apparatus according to claim 33 wherein the position regulating apparatus further includes stops that limit the range of motion of the second arm relative to the first arm, the dial indicator rotating through no more than one full rotation throughout the range of motion of the second arm relative to the first arm.

35. The apparatus according to claim 34 wherein:
the first arm comprises a mounting frame mountable in fixed relationship with the panel, the mounting frame including two hub portions each having a through opening;
the second arm constitutes a lever having first and second ends; and
the position regulating apparatus further comprising an axle through the lever and the through openings of the mounting frame to pivotably mount the first end of the lever on the mounting frame;
the cross arm being connected to the second end of the lever, and the trunion being mounted in the lever intermediate the first and second ends thereof.

36. The apparatus according to claim 35 further comprising:
a dial frame for the indicator dial and a key-and-slot connection between dial frame and trunion to mount the indicator dial on the trunion; and
a knob connected to the lead screw for manually turning the lead screw.

37. A combination comprising:
a volume controlling apparatus according to claim 25, and
a flexible venous reservoir comprising flexible walls defining a blood storage chamber, and an inlet and an outlet to the blood storage chamber defining a blood flow path through the blood storage chamber between the inlet and outlet.

38. Volume controlling apparatus for a flexible venous reservoir having flexible walls defining a blood storage chamber and an inlet and an outlet to the blood storage chamber defining a blood flow path through the blood storage chamber between the inlet and outlet, the volume controlling apparatus comprising:
a panel,
a pressure plate;
adjustable mounting means for movably mounting the pressure plate on the panel so that the flexible venous reservoir can be positioned between the panel and the pressure plate and in contact with both to adjustably limit the maximum volume of the flexible venous reservoir;

a dial indicator operatively connected to the adjustable mounting means so that the dial indicator rotates as the pressure plate is moved relative to the panel, the dial indicator being marked with indicia corresponding to the approximate maximum volume permitted in the flexible venous reservoir for various positions of the pressure plate relative to the panel.

39. The apparatus according to claim 38 wherein the dial indicator is operatively connected to the adjustable mounting means via a cable linkage.

40. The apparatus according to claim 39 further comprising drive means for driving the cable linkage to drive the adjustable mounting means to move the pressure plate relative to the panel.

41. The apparatus according to claim 38 wherein the dial indicator includes indicia along at least two scales corresponding to at least two flexible venous reservoirs having blood storage chambers of different sizes.

42. The apparatus according to claim 38 wherein the adjustable mounting means comprises:

a cross arm having one end connected to the pressure plate; and a position regulating apparatus for moving the cross arm relative to the panel and holding the cross arm in position, the position regulating apparatus comprising:
first and second arms pivotably connected together at one end of each of the first and second arms, the first arm being mounted to the panel and the second arm being mounted to the cross arm; and
a lead screw engaging the first and second arms to pivot the second arm relative to the first arm as the lead screw is turned to move the cross arm and pressure plate relative to the panel;
the dial indicator being operatively connected to the lead screw so that the dial indicator rotates as the lead screw is turned.

43. The apparatus according to claim 42 wherein:

the first arm comprises a mounting frame mountable in fixed relationship with the panel, the mounting frame including two hub portions each having a through opening;

the second arm constitutes a lever having first and second ends; and the position regulating apparatus further comprising an axle through the lever and the through openings of the mounting frame to pivotably mount the first end of the lever on the mounting frame;

the cross arm being connected to the second end of the lever, and the trunion being mounted in the lever intermediate the first and second ends thereof.

44. The apparatus according to claim 43 further comprising:

a dial frame for the indicator dial and a key-and-slot connection between dial frame and trunion to mount the indicator dial on the trunion; and a knob connected to the lead screw for manually turning the lead screw.

45. The apparatus according to claim 43 wherein the lead screw engages the second arm via a trunion that is pivotably mounted to the second arm so that the trunion maintains a constant orientation relative to the first arm as the lead screw is turned, the dial indicator being mounted to the trunion so that the dial indicator maintains a constant orientation relative to the first arm and panel as the second arm pivots relative to the first arm.

46. The apparatus according to claim 45 wherein the position regulating apparatus further includes stops that limit the range of motion of the second arm relative to the first arm, the dial indicator rotating through no more than one full rotation throughout the range of motion of the second arm relative to the first arm.

47. The apparatus according to claim 46 wherein the pressure plate is free to articulate relative to the adjustable mounting means to allow the pressure plate to self-level with respect to the flexible venous reservoir.

48. The apparatus according to claim 47 wherein the pressure plate is mounted to the cross arm by a ball-and-socket joint.

49. The apparatus according to claim 48 wherein the pressure plate is generally flat and has a generally circular configuration.

50. The apparatus according to claim 49 wherein the pressure plate is formed of transparent material.

51. A combination comprising:

a volume controlling apparatus according to claim 38; and a flexible venous reservoir comprising flexible walls defining a blood storage chamber, and an inlet and an outlet to the blood storage chamber defining a blood flow path through the blood storage chamber between the inlet and outlet.

* * * * *